(12) United States Patent
Voisin et al.

(10) Patent No.: US 12,423,467 B2
(45) Date of Patent: Sep. 23, 2025

(54) INDEX SEARCHING FOR CONSENT-PROTECTED PRIVATE HEALTHCARE DATA

(71) Applicant: Google LLC, Mountain View, CA (US)

(72) Inventors: Craig Douglas Voisin, Mississauga (CA); Truc Duc Le, Kitchener (CA); Marwan Elsayed Abdelaal Tammam Issa, Waterloo (CA); Xiao Yang, Richmond Hill (CA); Jianpeng Chao, Waterloo (CA); Kalyan Srinivas Pamarthy, Sunnyvale, CA (US); Robert Lou, Sunnyvale, CA (US); Milena Bukal, Mountain View, CA (US)

(73) Assignee: Google LLC, Mountain View, CA (US)

( * ) Notice: Subject to any disclaimer, the term of this patent is extended or adjusted under 35 U.S.C. 154(b) by 154 days.

(21) Appl. No.: 18/063,679

(22) Filed: Dec. 8, 2022

(65) Prior Publication Data
US 2024/0193299 A1 Jun. 13, 2024

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC .............. G06F 21/62–6245; G16H 10/60
See application file for complete search history.

(56) References Cited

U.S. PATENT DOCUMENTS

| 10,467,306 B2* | 11/2019 | Shah | G06F 16/2457 |
| 2007/0240203 A1* | 10/2007 | Beck | G16H 10/60 |
| | | | 726/4 |
| 2014/0143837 A1 | 5/2014 | Fletcher et al. | |
| 2014/0297666 A1* | 10/2014 | Morris | G06Q 10/109 |
| | | | 707/754 |

(Continued)

OTHER PUBLICATIONS

"Access tokens in the Microsoft identity platform", Microsoft, Jun. 10, 2024, 13 pp.

(Continued)

*Primary Examiner* — Jonathan A Bui
(74) *Attorney, Agent, or Firm* — Shumaker & Sieffert, P.A.

(57) ABSTRACT

A method of index searching of consent-protected private healthcare data includes receiving, from a computing device, a search request for access to consent-protected healthcare data stored at a consent-indexed healthcare data store. The request includes one or more consent parameters asserted for a user of the computing device. The method also includes identifying one or more asserted access consent scenarios for accessing the requested consent-protected healthcare data based on the one or more consent parameters, each asserted access consent scenario of the one or more asserted access consent scenarios representing a respective subset of the one or more consent parameters. The method further includes defining a search filter based on the one or more asserted access consent scenarios and determining, via an indexed search of the data store using the search filter, a subset of the requested data. The method includes providing the subset of data to the computing device.

20 Claims, 9 Drawing Sheets

| ResourceID | PERMIT | DENY | Other fields | |
|---|---|---|---|---|
| 1 | actor1\|\*\|\*<br>actor1\|purpose1\|\* | actor1\|purpose1\|env1 | blah | ←300a |
| 2 | actor1\|\*\|\*<br>actor2\|\*\|\* | actor2\|\*\|env2 | foo | ←300b |
| 3 | | actor3\|\*\|\* | bar | ←300c |
| ⋮ | ⋮ | ⋮ | ⋮ | |

(56) References Cited

U.S. PATENT DOCUMENTS

| | | | | |
|---|---|---|---|---|
| 2016/0026717 | A1* | 1/2016 | Kelsey | H04L 67/30 |
| | | | | 707/754 |
| 2017/0169116 | A1* | 6/2017 | Shah | G06F 16/248 |
| 2017/0201508 | A1* | 7/2017 | Beck | G06F 21/31 |
| 2018/0046753 | A1 | 2/2018 | Shelton | |
| 2018/0233225 | A1 | 8/2018 | Experton et al. | |
| 2018/0247072 | A1* | 8/2018 | Hind | G06F 21/6227 |
| 2018/0248886 | A1* | 8/2018 | Hind | G06F 16/9538 |
| 2018/0276341 | A1 | 9/2018 | Rab et al. | |
| 2020/0126663 | A1* | 4/2020 | Lucas | G06V 30/19013 |
| 2021/0012882 | A1* | 1/2021 | Lefkofsky | G16H 50/70 |
| 2021/0090694 | A1* | 3/2021 | Colley | G16H 15/00 |
| 2022/0076794 | A1 | 3/2022 | Woodlief et al. | |
| 2022/0319645 | A1* | 10/2022 | Scipioni | G06F 21/6245 |

OTHER PUBLICATIONS

"Fhir-proxy", GitHub, Retrieved from: https://github.com/microsoft/fhir-proxy, Mar. 2022, 8 pp.

Balter et al., "Privacy in Medical Systems using FHIR", Microsoft Learn, Mar. 1, 2022, 16 pp.

International Search Report and Written Opinion of International Application No. PCT/US2023/082791 dated Mar. 19, 2024, 9 pp.

Weave et al., "Azure API for FHIR access token validation", Microsoft Learn, Sep. 24, 2024, 4 pp.

Weave et al., "Microsoft Entra identity configuration for Azure API for FHIR", Microsoft Learn, Sep. 24, 2024, 5 pp.

Weave et al., "Overview of search in Azure API for FHIR", Microsoft Learn, Oct. 6, 2024, 8 pp.

* cited by examiner

```
600 ─┐
     ↘ where ...
            and (
                (
                        PERMIT contains any of {
                            "actor1|purpose1|env1",
                            "actor1|purpose1|*",
                            "actor1|*|env1",
                            "actor1|*|*",
                            // no any actor
                        }
                        and DENY does not contain any
        of {
                            "actor1|purpose1|env1",
                            "actor1|purpose1|*",
                            "actor1|*|env1",
                            "actor1|*|*",
                            // no any actor
                        }
                )
            )
```

INDEX SEARCHING FOR CONSENT-PROTECTED PRIVATE HEALTHCARE DATA

TECHNICAL FIELD

This disclosure relates to index searching for consent-protected private healthcare data.

BACKGROUND

The healthcare industry uses consent as a standard for how a patient, or a representative for the patient, can permit or deny access to the patient's private healthcare data. In particular, the patient, or the patient's representative, can specify consent directives that define which particular entities, for which particular purposes, from which particular environments, and during which particular time periods may access particular portions of the patient's private healthcare data.

SUMMARY

One aspect of the disclosure provides a computer-implemented method executed by data processing hardware that causes the data processing hardware to perform operations. The operations include receiving, from a computing device, a search request for access to consent-protected healthcare data stored at a consent-indexed healthcare data store in communication with the data processing hardware. The search request includes one or more consent parameters asserted for a user of the computing device. The operations include identifying one or more asserted access consent scenarios for accessing the requested consent-protected healthcare data based on the one or more consent parameters. Each respective asserted access consent scenario of the one or more asserted access consent scenarios represent a respective subset of the one or more consent parameters. The operations also include defining a search filter based on the one or more asserted access consent scenarios and determining, via an indexed search of the consent-indexed healthcare data store using the search filter, a subset of the requested consent-protected healthcare data permitted for the user to access. The operations include providing, to the computing device, the subset of the requested consent-protected healthcare data.

Implementations of the disclosure may include one or more of the following optional features. In some implementations, the one or more consent parameters represent at least one of an actor identifier for the user, a purpose identifier for requesting the requested consent-protect healthcare data, an environment identifier identifying an environment for the user, or a timestamp indicating a time/date of the search request. The one or more consent parameters may be provided by the user via the computing device and/or determined by the data processing hardware based on one or more attributes of the user or the computing device. In some examples, the consent-indexed healthcare data store includes a plurality of healthcare data records indexed based on consent scenarios. In some of these examples, each consent scenario of the consent scenarios represents two or more of an actor, a purpose, an environment, or a time period.

In some implementations, the consent-indexed healthcare data store includes a plurality of healthcare data records. Each healthcare data record of the plurality of healthcare data records includes a respective permit field defining one or more respective access consent scenarios that permit access to the healthcare data record and a respective deny field defining one or more respective access consent scenarios that deny access to the healthcare data record. In some of these implementations, each asserted access consent scenario of the plurality of asserted access consent scenarios represents two or more of an actor, a purpose, an environment, or a time period.

Optionally, the request includes an indication that an identity of the user of the computing device has been authenticated and a fast healthcare interoperability resources (FHIR) application programming interface (API) token including the one or more consent parameters. The operations may further include, in response to receiving the request, re-authenticating the identity of the user of the computing device. Additionally or alternatively, the operations may further include providing a proxy to convert the FHIR API token to a hypertext transfer protocol (HTTP)-based consent header. In some examples, the operations further include determining that particular healthcare data of the requested consent-protected healthcare data is included within the subset when the indexed search both permits and denies access to the particular consent-protected healthcare data.

Another aspect of the disclosure provides a system for performing index searching for consent-protected private healthcare data. The system includes data processing hardware and memory hardware in communication with the data processing hardware. The memory hardware stores instructions that when executed on the data processing hardware cause the data processing hardware to perform operations. The operations include receiving, from a computing device, a request for access to consent-protected healthcare data stored at a consent-indexed healthcare data store in communication with the data processing hardware. The request includes one or more consent parameters provided to the computing device by a user of the computing device. The operations include identifying one or more asserted access consent scenarios for accessing the requested consent-protected healthcare data based on the one or more consent parameters. Each respective asserted access consent scenario of the one or more asserted access consent scenarios represent a respective subset of the one or more consent parameters. The operations also include defining a search filter based on the one or more asserted access consent scenarios and determining, via an indexed search of the consent-indexed healthcare data store using the search filter, a subset of the requested consent-protected healthcare data permitted for the user to access. The operations include providing, to the computing device, the subset of the requested consent-protected healthcare data.

Implementations of the disclosure may include one or more of the following optional features. In some implementations, the one or more consent parameters represent at least one of an actor identifier for the user, a purpose identifier for requesting the requested consent-protect healthcare data, an environment identifier identifying an environment for the user, or a timestamp indicating a time/date of the search request. The one or more consent parameters may be provided by the user via the computing device and/or determined by the data processing hardware based on one or more attributes of the user or the computing device. In some examples, the consent-indexed healthcare data store includes a plurality of healthcare data records indexed based on consent scenarios. In some of these examples, each consent scenario of the consent scenarios represents two or more of an actor, a purpose, an environment, or a time period.

In some implementations, the consent-indexed healthcare data store includes a plurality of healthcare data records. Each healthcare data record of the plurality of healthcare data records includes a respective permit field defining one or more respective access consent scenarios that permit access to the healthcare data record and a respective deny field defining one or more respective access consent scenarios that deny access to the healthcare data record. In some of these implementations, each asserted access consent scenario of the plurality of asserted access consent scenarios represents two or more of an actor, a purpose, an environment, or a time period.

Optionally, the request includes an indication that an identity of the user of the computing device has been authenticated and a fast healthcare interoperability resources (FHIR) application programming interface (API) token including the one or more consent parameters. The operations may further include, in response to receiving the request, re-authenticating the identity of the user of the computing device. Additionally or alternatively, the operations may further include providing a proxy to convert the FHIR API token to a hypertext transfer protocol (HTTP)-based consent header. In some examples, the operations further include determining that particular healthcare data of the requested consent-protected healthcare data is included within the subset when the indexed search both permits and denies access to the particular consent-protected healthcare data.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

For clarity of description, disclosed implementations are described with reference to access control for consent-protected private healthcare data (also referred to herein as healthcare data). However, persons of ordinary skill in the art will recognize that disclosed implementations are also applicable to access control for other types of protected data such as, but not limited to, financial data, research data, industrial data, manufacturing data, and government data. In disclosed implementations, consent directives include one or more of actor (i.e., who—a doctor, a pharmacist, a professor, a researcher, a diagnostician, a technician, an insurance representative, a billing professional, etc.), purpose (i.e., why—billing, diagnosis, emergency care, urgent care, office visit, triage, treat, examine, test, research, etc.), environment (i.e., from where—a business, a doctor office, a medical facility, a laboratory, a research organization, an insurance company, a government, a country, a geographic area, etc.), and time period. However, persons of ordinary skill in the art will also recognize that disclosed implementations can be used to control access to data based on additional or alternative constraints. Furthermore, for clarity of description, disclosed implementations are described with reference to a patient providing consent directives for the patient's private healthcare data. However, persons of ordinary skill in the art will recognize that disclosed implementations also permit a duly authorized person (e.g., a guardian, a person with power of attorney, a judge, etc.) to provide consent directives for another person's healthcare data. Further still, while disclosed implementations control access to a patient's private healthcare data based on the patient's consent directives, disclosed systems may additionally provide access to the patient's private healthcare data outside of the patient's consent directive. For example, an emergency department at a hospital may always have access to a patient's private healthcare data regardless of any consent directives to the contrary.

Traditionally, enforcing consent-based data access control for healthcare data has been problematic because malicious actors may easily attack healthcare data storage systems using illegitimate asserted consent scenarios (i.e., alleged illegitimate combinations of actor, purpose, environment, and/or time period). For example, a person may allege they are a licensed doctor when they are not. Moreover, consent directives need to be fine-grained such that different portions of a patient's healthcare data (i.e., different healthcare data records, different segments of healthcare records, etc.) may be accessed only under different consent scenarios. Furthermore, different patients may have different consent directives. Accordingly, consent-based data access control for healthcare data cannot be performed using system-level access control (e.g., user authentication). For example, traditional user authentication systems like a Keycloak system, an Okta® system, a Cloud Identifier system, an identity and management (IAM) system, a substitutable medical application, and reusable technology (SMART) on fast healthcare interoperability resources (FHIR) system rely on administrators to set access rules. Furthermore, certain FHIR operations can be prohibitively expensive to perform. For example, consider an FHIR user who is a licensed doctor doing medical research and desires to obtain all available medical records related to diabetes. A traditional search engine first identifies and pulls all records related to all diabetic patients, the number of which may be very large (e.g., millions), and then has to process each and every individual record to ensure the doctor has consent to access the record. Such a process does not scale to very large contemporary healthcare data stores, such as a data store storing thousands of millions of records, or zettabytes (ZB) of data (i.e., $10^{21}$ bytes or equivalently 10,000 billion terabytes (TB)). Some experts predict that, by the year 2025, the healthcare industry will generate—463 exabytes (EB) (i.e., $10^{18}$ bytes or equivalently 10 billion TB) of healthcare data each day. Further still, a search engine has to be able to resolve conflicts when applicable permit and deny consents conflict. However, using "deny always wins," may not reflect the intention of the patient(s). For example, a patient may deny access to everyone but permit the patient's spouse access to the patient's blood-pressure data while denying the patient's spouse access to other healthcare data of the patient. Accordingly, there is a need for methods of enforcing access control for consent-protected private healthcare data access control that are secure, consistent, compliant, and scalable.

Disclosed implementations solve these, and potentially other problems by indexing each healthcare data record in a consent-protected healthcare data store with the respective consent attributes (e.g., actor, purpose, environment, and/or time period) for the healthcare data record. The consent-indexed healthcare data records can then be efficiently searched for using index-based searching based on a particular asserted access consent scenario (e.g., an asserted combination of actor, purpose, environment, and time period) provided by a user who is attempting to access the consent-indexed healthcare data records. As used herein, "asserted access consent scenario" may refer to a particular combination of actor, purpose, environment, and time period that an accessee asserts/alleges is legitimate for the purpose of accessing consent-protected healthcare data. In disclosed examples, the indexed consent attributes include both permit and deny consent attributes. For example, indexed consent attributes can reflect that access is permitted to any person (i.e., who) at particular environments (i.e., where) (e.g., a medical research entity) doing research (i.e., purpose) for the next 6 years (i.e., time period), while denying access to everyone else.

Figure 1:
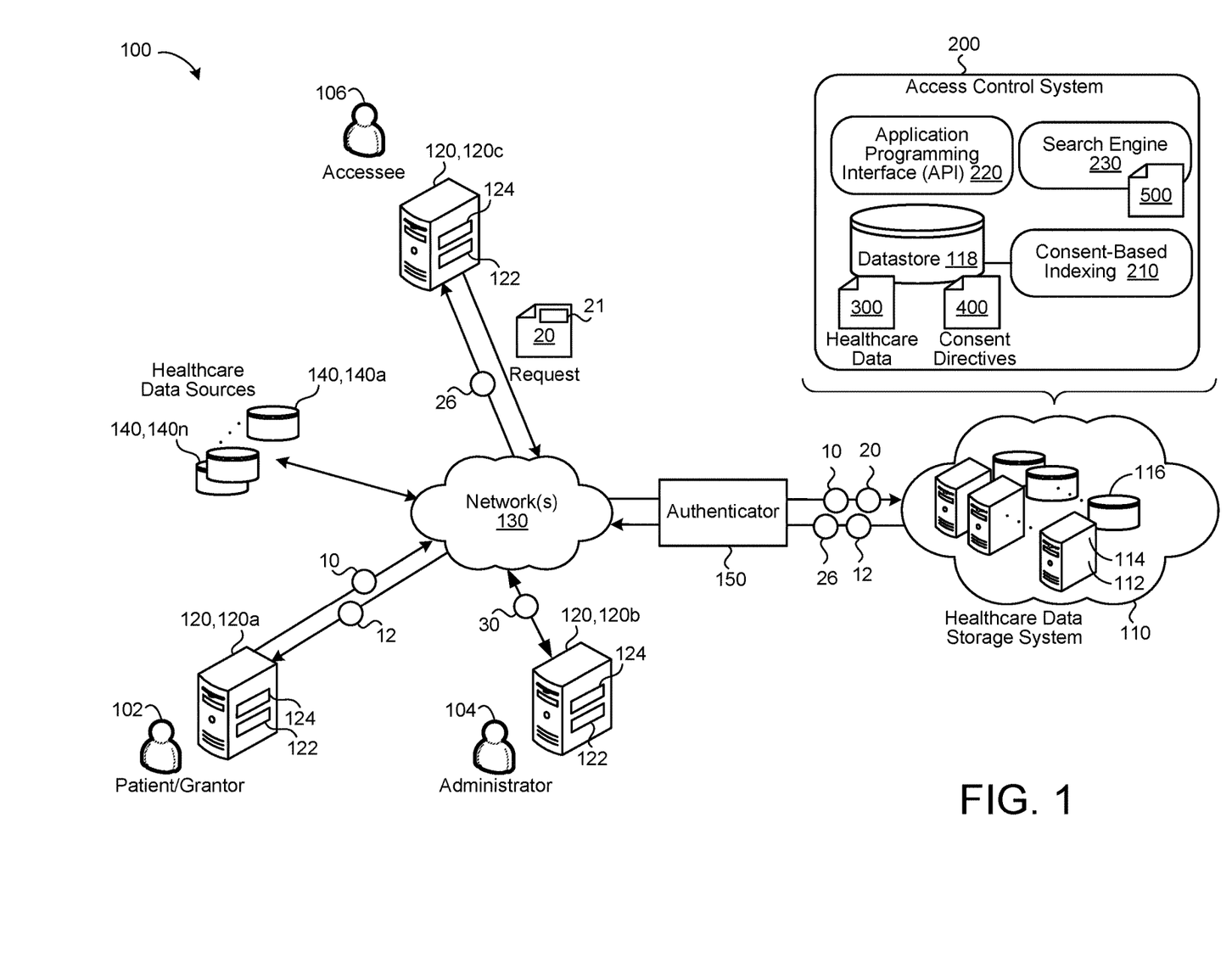
FIG. 1 is a schematic view of an example healthcare data system for performing index searching for consent-protected healthcare data.

FIG. 1 is a schematic view of an example healthcare data system 100 (also referred to herein as system 100) that includes a healthcare data storage system 110 (also referred to herein as storage system 110) in communication with one or more computing devices 120, 120a-n via any number and/or type(s) of private and/or public networks 130. In the illustrated example, the storage system 110 includes a cloud-based computing environment having scalable/elastic resources 112 including computing resources 114 (e.g., data processing hardware) and/or storage resources 116 (e.g., memory or non-volatile storage hardware). Alternatively, the storage system 110 may include a single computing device, or multiple computing devices at the same and/or different locations. The storage system 110 may include a data store 118 overlain on the storage resources 116 to allow scalable use of the storage resources 116 by the computing resources 114. The computing devices 120 may correspond to any computing device, such as a server, a desktop computer, a laptop, a tablet, or a mobile device (e.g., a smart phone, or smart wearable). The computing devices 120 each include respective computing resources 122 (e.g., data processing hardware) and/or respective storage resources 124 (e.g., memory hardware).

Figure 2:
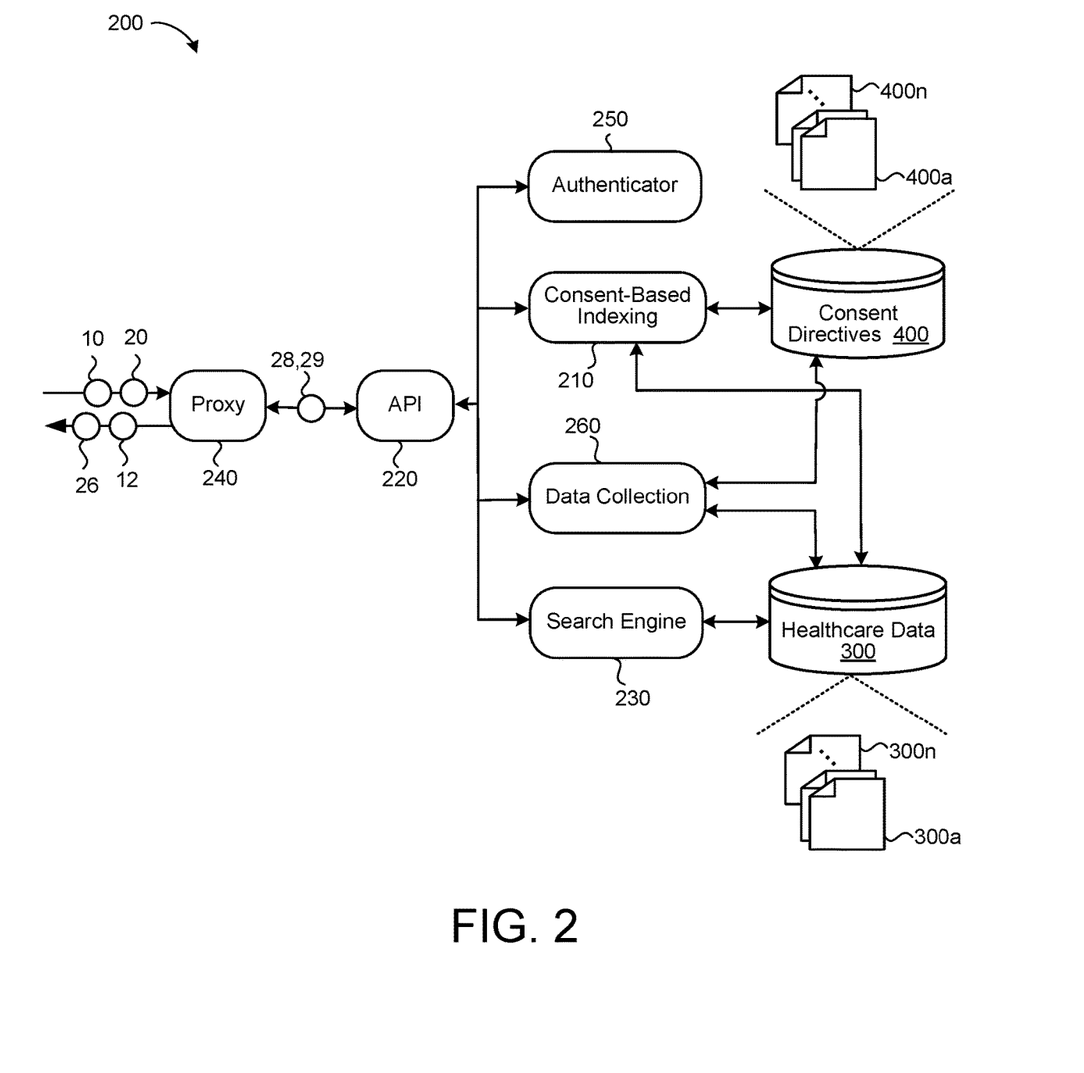
FIG. 2 is a schematic view of an example of the healthcare data storage system of FIG. 1.
Figure 3:
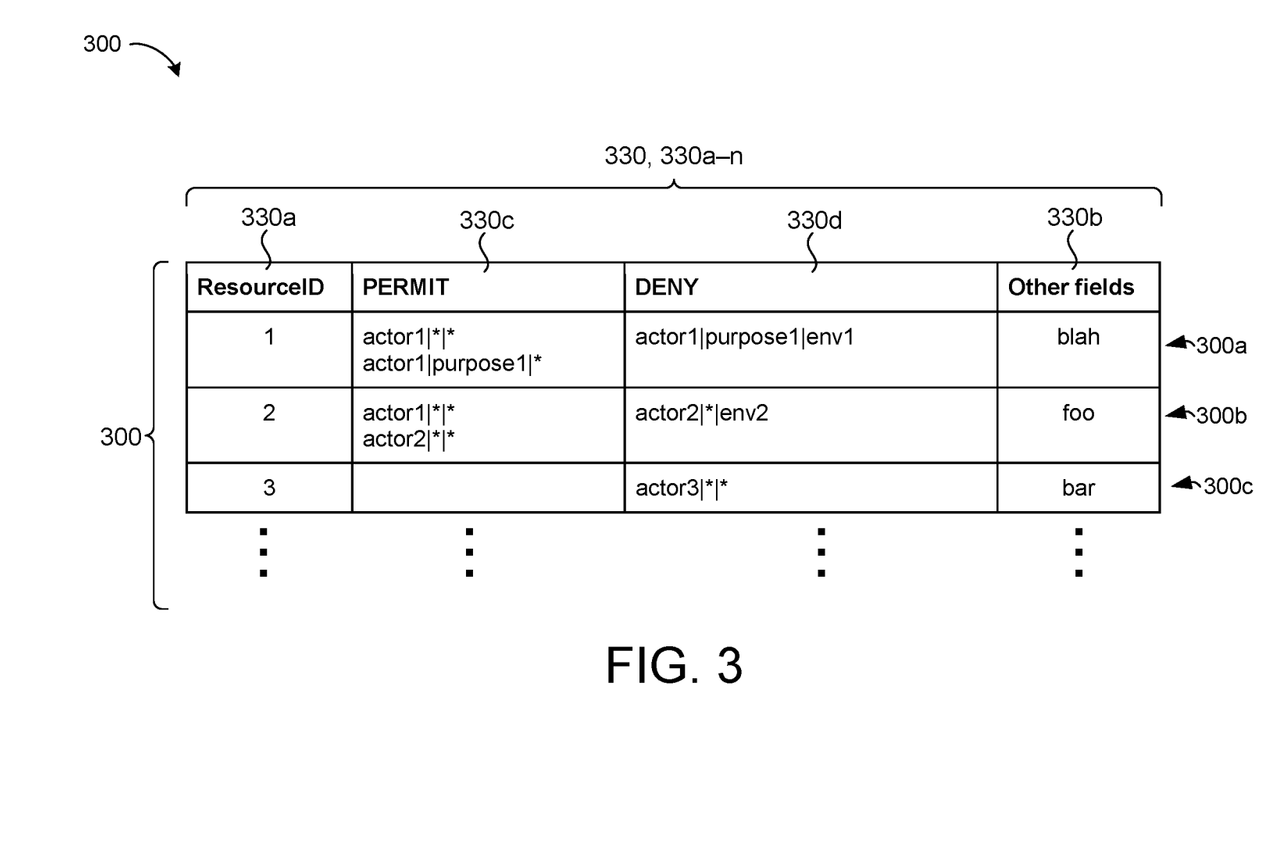
FIG. 3 is a table depicting an example data structure for storing the consent-indexed healthcare data of FIGS. 1 and 2.

The storage system 110 executes an access control system 200 to control access to consent-protected healthcare data 300 (also referred to herein as healthcare data 300, and consent-indexed healthcare data 300) based on asserted access consent scenarios. As shown in FIGS. 2 and 3, the healthcare data 300 includes any number and/or type(s) of healthcare data records 300, 300a-n (also referred to herein as data records 300) for any number of patients. A patient may have any number and/or type(s) of associated records 300, and different patients may have different numbers of records 300. Each data record 300 is associated with a particular patient, or a particular set of patients (e.g., a couple undergoing fertility treatment, medical research results for a group of patients, etc.). When a data record 300 is associated with multiple patients, each patient may have their own applicable consent directives 400 for the data record 300 as a whole and/or only their portion(s) of the data record 300. Moreover, a data record 300 may also be associated with a person or organization (e.g., private or governmental) that originally collected or owns the healthcare data of the data record 300. The healthcare data 300 may be stored in the datastore 118 overlain on the storage resources 116.

Each data record 300 of the plurality of healthcare data records 300 includes a plurality of fields 330, 330a-n. For each data record 300, a resource identifier (ID) field 330a stores a respective ID that uniquely identifies the data record 300, and one or more data fields 330, 330b that store the data content portion of the data record 300. For example, the actual healthcare data, patient information, etc. for the data record 300.

The fields 330 for each data record 300 also include a permit field 330c and a deny field 330d that define, respectively, permitted and denied consent scenario(s) for the data record 300. The permit field 330c of each data record 300 may store one or more indexed permit consent attributes that define respective consent scenarios (e.g., combinations of who, purpose, environment and time period) under which respective healthcare data 330b of the data record 300 can be accessed. For example, the permit field 330c for data record 300b indicates that actor1 and actor2 can access healthcare data stored in the data fields 330b of the data record 300b for any purpose and from any environment. The deny field 330d of each data record 300 may store one or more indexed deny consent attributes that define respective consent scenarios (e.g., combinations of who, purpose, environment and time period) under which access to respective healthcare data stored in the data fields 330b of the data record 300 is denied. For example, the deny field 330d for data record 300c indicates that actor3 cannot access healthcare data stored in the data fields 330b of the data record 300c regardless of purpose or environment. In some examples, a permit consent attribute and/or a deny consent attribute may apply to only a portion of the healthcare data stored in the data fields 330b of a data record 300.

While an example data structure in the form of a table for storing the consent-protected healthcare data 300 is shown in FIG. 3, the table may have additional or alternative fields storing the same, different, additional, or alternative data, and may be arranged in any other way. Moreover, the consent-protected healthcare data 300 may be stored using other types of data structures.

Figure 4:
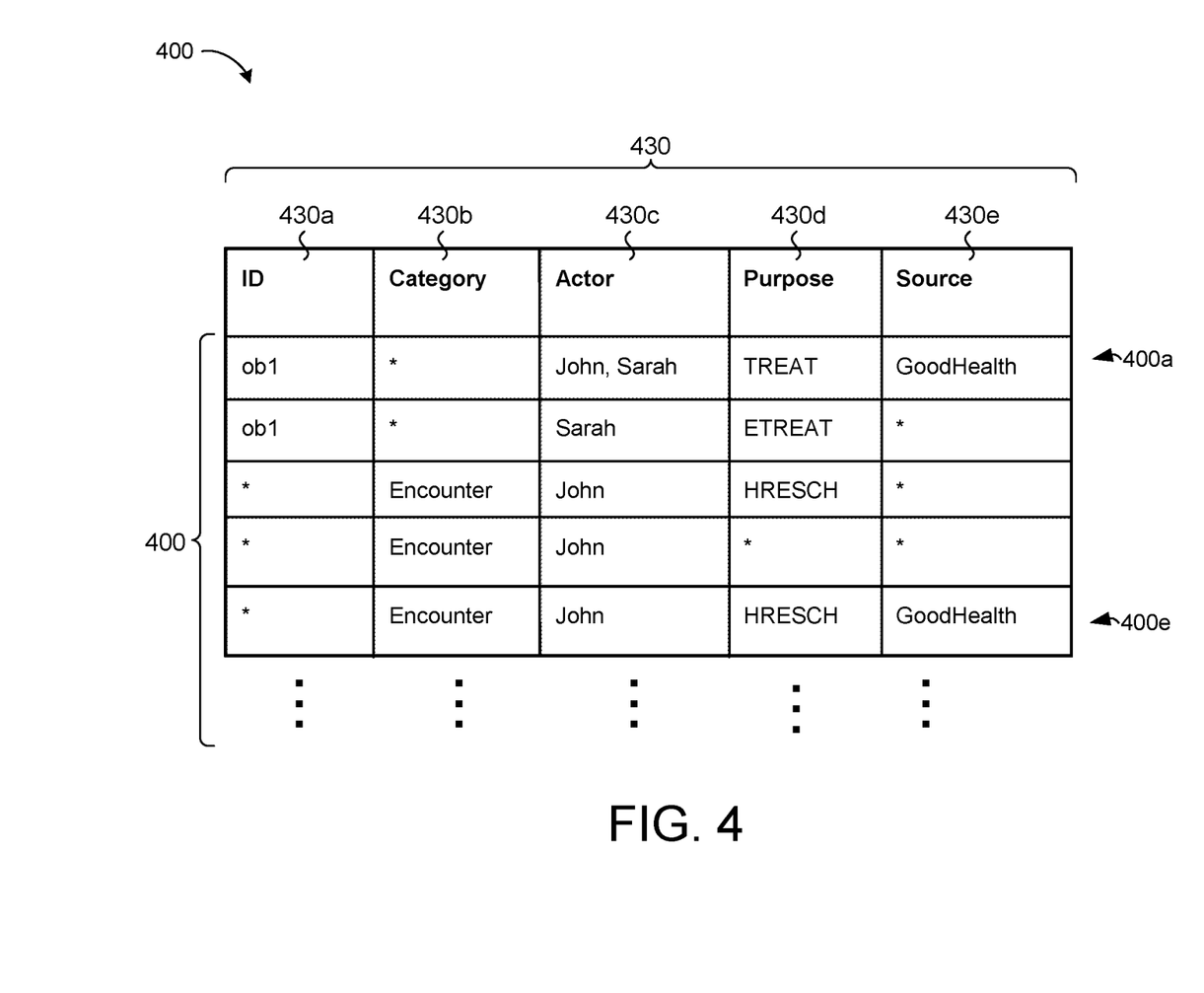
FIG. 4 is a table depicting an example data structure for storing the consent directives of FIGS. 1 and 2.

Referring back to FIG. 1, the access control system 200 executes consent-based indexing 210 to (re-)index each data record 300 to determine the respective content for the respective permit field 330c and the respective deny field 330d for the data record 300. The access control system 200 (re-)indexes each data record 300 based on applicable ones of a plurality of consent directives 400 corresponding to the patient associated with the data record 300. As shown in FIGS. 2 and 4, the consent directives 400 includes any number and/or type(s) of consent directives 400, 400a-n for any number of patients. A patient may have any number and/or type(s) of associated consent directives 400, and different patients may have different numbers of consent directives 400. The consent directives 400 may include consent directives from other entities. For example, a person or organization (e.g., private or governmental) that originally collected or owns healthcare data 300 may provide consent directives 400 for their collected or owned data. Such consent directives 400 may be in addition to, or instead of any consent directives 400 defined by the patient(s) associated with such healthcare data 300. The consent directives 400 may also include default consent directives 400 that apply by default to all healthcare data records 300 absent patient-defined consent directives 400. In some examples, default consent directives 400 are defined by, for example, an administrator, rules, laws, and government directives. In general, consent directives 400 may be provided by any type of entity that has right of ownership or control of particular healthcare data 300. Because consent directives 400 may be defined by different entities, the resulting consent-index healthcare data 300 may reflect a blending of similar or conflicting consent directives 400 from any number and/or type(s) of such entities. Such a blending of consent directives 400 may occur at the time the healthcare data 300 is indexed, and/or at a time when the consent-indexed healthcare data 300 is searched. Each consent directive 400 defines one or more consent scenarios for which access to data is permitted. Each consent directive 400 is associated with a particular patient (i.e., defined by the patient or a representative for the patient), such that each consent directive 400 only applies to that patient's healthcare data 300. The consent directives 400 may be stored on the datastore 118 overlain on the storage resources 116.

In some examples, the consent-based indexing 210 processes healthcare data 300 as the healthcare data 300 is ingested into the healthcare data storage system 110. That is, as received from any number and/or type(s) of healthcare data sources 140, 140*a-n*. Example healthcare data sources 140 are associated with, but not limited to, doctor's offices, medical groups, hospitals, clinics, and medical research organizations. Alternatively, the consent-based indexing 210 processes batches of ingested healthcare data 300. In some implementations, the consent-based indexing 210 processes the healthcare data 300 as each consent directive 400 is added, changed, and/or deleted (see below). Alternatively, the consent-based indexing 210 processes the healthcare data 300 based on batches of added, changed, and/or deleted consent directives 400.

Each consent directive 400 of the plurality of consent directives 400 includes a plurality of fields 430, 430*a-n*. For each consent directive 400, an ID field 430*a* may store one or more IDs of corresponding particular healthcare data records 300 (e.g., corresponding to an ID 330*a*) to which the consent directive 400 applies. Otherwise, the ID field 430*a* may store the "*" symbol (or some other wildcard symbol) to indicate that the consent directive 400 applies to all the patient's healthcare data records 300. A category field 430*b* of each consent directive 400 may define one or more categories of healthcare data to which the consent directive 400 applies. For example, the category field 430*b* of the consent directive 400*e* indicates that all healthcare data related to an encounter with a medical doctor is permitted. Otherwise, the category field 430*b* may store the "*" symbol (or some other wildcard symbol) to indicate that the consent directive 400 applies to all categories of healthcare data records 300.

The fields 430 for each consent directive 400 include a respective set of consent definition fields 430, 430*c-e* that define the consent scenario(s) for each consent directive 400. An actor field 430*c* may define which actors have access, a purpose field 430*d* may define for which purposes healthcare data may be accessed, and a source field 430*e* may define from which environments healthcare data may be accessed. The fields 430*e-e* may store particular values or may, alternatively, store a wildcard symbol (e.g. "*").

While an example data structure in the form of a table for storing the consent directives 400 is shown in FIG. 4, it should be appreciated that the table may have additional or alternative fields storing the same, different, additional, or alternative data, and may be arranged in any other way. Moreover, the consent directives 400 may be stored using other types of data structures, such as the graph 500 of FIG. 5.

Figure 5:
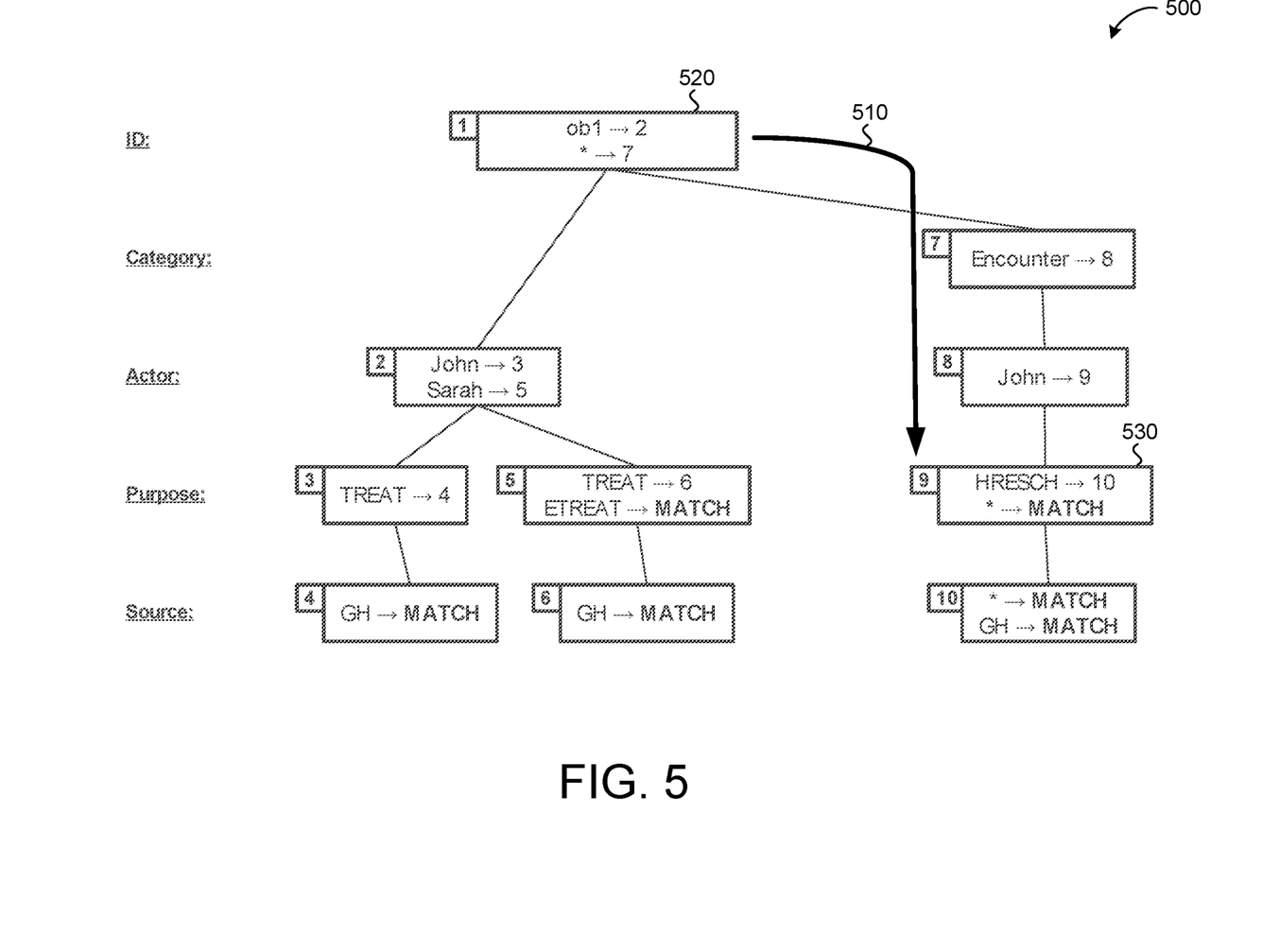
FIG. 5 is a graph depicting another example data structure for storing the consent directives of FIGS. 1 and 2.

FIG. 5 is another example data structure in the form of a graph 500 for representing a set of consent directives 400. The example graph 500 represents a set of example consent directives 400 similar to the example consent directives 400 of FIG. 4. A representation of such a graph may be determined and stored for each healthcare data record 300 instead of the permit field 330*c* and the deny field 330*d* (see FIG. 3). In the example graph 500, each consent attribute is a node, and a path from a root node to a child node (e.g., a path 510 from root node 520 to a child node 530) represents an AND-relationship of all consent attributes along the path. Sibling nodes of the same level represent an OR-relationship of the values of the consent attributes at that level. At search time, the parameters of an asserted consent scenario can be used to trace the graph 500 to determine whether the asserted consent scenario is permitted to access particular healthcare data records 300. The complexity of tracing the graph 500 is of order k=O(graph depth)=O(number of consent attributes), where k may be small and constant (e.g., 4) in practice (e.g. actor, purpose, environment, resource type, resource ID, resource's source, resource's tag, etc.). Overall, at index time, for a patient who has N consent directives 400 and M healthcare data records 300, the number of operations to trace the graph 500 is of order O(k*M). In contrast, to directly search the table of FIG. 3 requires a number of operations of order O(N*M).

In some examples, the graph 500 is constructed by creating an initial tree having a path corresponding to each applicable consent directive 400, removing repeated/redundant paths that end at a same node to compress the tree (e.g., repeated subtrees), and converting the compressed tree to a directed graph.

Returning to FIG. 1, the consent-based indexing 210 indexes a particular data record 300 associated with a particular patient 102 by obtaining the consent directives 400 that are associated with the patient 102 and applicable to the data record 300. For example, if the data fields 330*b* of the data record 300 contain blood test results, then the consent-based indexing 210 identifies the patient's consent directives 400 that are related to blood test results or, alternatively, all types of healthcare data. The consent-based indexing 210 then creates any number of (including possibly zero) permit consent scenarios based on logical combinations of the consent definition fields 430*c-e* of each identified consent directive 400 and stores the created permit consent scenarios in the respective permit field 330*c* for the data record 300. In some examples, the consent-based indexing 210 also creates deny consent scenarios that are based on logical negatives of the created permit consent scenarios and stores them in the respective deny field 330*d* for the data record 300. Alternatively, if a graph, such as the graph 500, is used to derive permit and/or deny consent scenarios, the consent-based indexing 210 creates the graph based on the consent directives 400 that are associated with the patient 102 and applicable to the data record 300, and uses the graph to populate the permit field 330c and/or the deny field 330d for the data record 300.

The access control system 200 executes an application programming interface (API) 220 to control access to the access control system 200 by the computing devices 120. In some examples, the API 220 is implemented in accordance with the fast healthcare interoperability resources (FHIR) API, and search requests are FHIR API search requests.

In the example shown, a patient 102, or a representative of the patient 102 (e.g., a grantor), uses a computing device 120a to interact with the API 220 to provide patient inputs 10 for providing, updating, or deleting patient's respective consent directives 400. In response to the patient inputs 10, the access control system 200 may provide one or more patient outputs 12 to the patient 102 via the computing device 120a indicating whether or not the requested changes to the patient's consent directives 400 have been made.

In some examples, an administrator 104 uses a computing device 120b to interact with the access control system 200 to configure/administer the access control system 200. For example, the administrator 104 may provide administrator inputs 30 that define/specify what powers are delegated to a patient or the patient's representative) for creating the patient's consent directives 400. For instance, the administrator may provide administrator inputs 30 that define what types of consent directives 400 a patient is allowed to define/create and/or what types of consent scenarios persons seeking access to the healthcare data 300 are allowed to assert. For example, the administrator 104 may require that an asserted actor be an authenticated user of the access control system 200 and/or may define a restricted list of purposes, environments, and/or time periods that may be selected from or used in defining consent directives 400 and/or when requesting access. The administrator 104 may also define default consent directives 400.

The access control system 200 executes a search engine 230 to execute indexed searches of the consent-indexed healthcare data 300. In response to a search request 20 requesting access to some of the consent-protected healthcare data 300, the search engine 230 performs index-based searching on the healthcare data 300 based on one or more particular access consent scenarios asserted by, or associated with a person (i.e., an accessee 106) as part of the search request 20. Here, the accessee 106 accesses the healthcare data 300 using a computing device (e.g., the computing device 120c) via the API 220, and provides the search request 20 including one or more consent parameters 21 that represent one or more asserted access consent scenarios for the search request 20. In some instances, the accessee 106 is associated with different possible access consent scenarios. The accessee 106 may be associated with different consent scenarios at different times. The consent parameters 21 may include/indicate at least one of an actor identifier for the accessee 106 providing the search request 20, a purpose identifier for requesting healthcare data, an environment identifier identifying an environment for the accessee 106, or a timestamp indicating a time/date of the search request 20. For example, the accessee 106 may be both a licensed doctor and a medical researcher and, the accessee 106 may provide one or more actor identifiers asserting one or both of the accessee's roles as part of the search request 20. Additionally or alternatively, the actor identifier may simply include one or more user identifiers (e.g., a user ID and authentication credentials) that uniquely identifies the accessee 106 and that the access control system 200 may use to determine what actor and/or what type of actor the accessee 106 pertains to. An accessee 106 may also have different purposes or be associated with different environments (e.g., a hospital, a research facility, and/or a geographic area) for accessing the healthcare data 300 at different times. In some implementations, the API 220 asserts consent parameters on behalf of the accessee 106 based upon one or more attributes of the accessee 106 and/or the computing device 120c. For example, the API 220 may, based on the accessee's Internet protocol (IP) address, determine an environment associated with the accessee 106 and add that determined environment to the consent parameters 21 asserted by the accessee 106. Notably, such an added consent parameter 21 may cause the accessee 106 to be unable to obtain any of the healthcare data 300. For example, an added consent parameter 21 may represent a particular country for which access to the healthcare data 300 is denied by default. In some examples, the API 220 checks the consent parameters 21 against a list of restricted purposes, environments, and/or time periods provided by the administrator 104. Additionally, the API 220 may map the consent parameters 21 to a list of available actors, purposes, environments, and/or time periods used by the consent-based indexing 210 when indexing the healthcare data 300. In some examples, the API 220 checks asserted consent scenarios to ensure they comply with regulatory and legal requirements.

The search engine 230 generates a search filter 600 (see FIG. 6) based on the indicated asserted access consent scenario(s). The search engine 230 uses the generated search filter to perform a search of the indexed permit field 330c and the indexed deny field 330d. The search engine 230 identifies any records 300 that the accessee 106 is (a) consented to access based on the permit field 330c and (b) not denied access based on the deny field 330d. Results 26 (e.g., a subset including some or all of the consent-protected healthcare data 300 requested by the search request 20 that the accessee 106 is permitted to access) identified by the search engine 230 are returned by the access control system 200 to the computing device 120c via the API 220. Alternatively, as discussed above, the search filter 600 may perform an indexed search of the healthcare data 300 using a graph such as the example graph 500 of FIG. 5.

In some examples, when an accessee 106 is both permitted to access a particular record 300 and denied access to the record 300, the search engine 230 does not provide the respective healthcare data 300 of the record 300 to the accessee 106. However, alternatively, such conflicts may be resolved using other methods or logic, such as by a person authorized to resolve conflicts. Such a person may also be responsible for conducting audits, legal reviews, regulatory compliance, and ethics for the healthcare data storage system 110.

Figure 6:
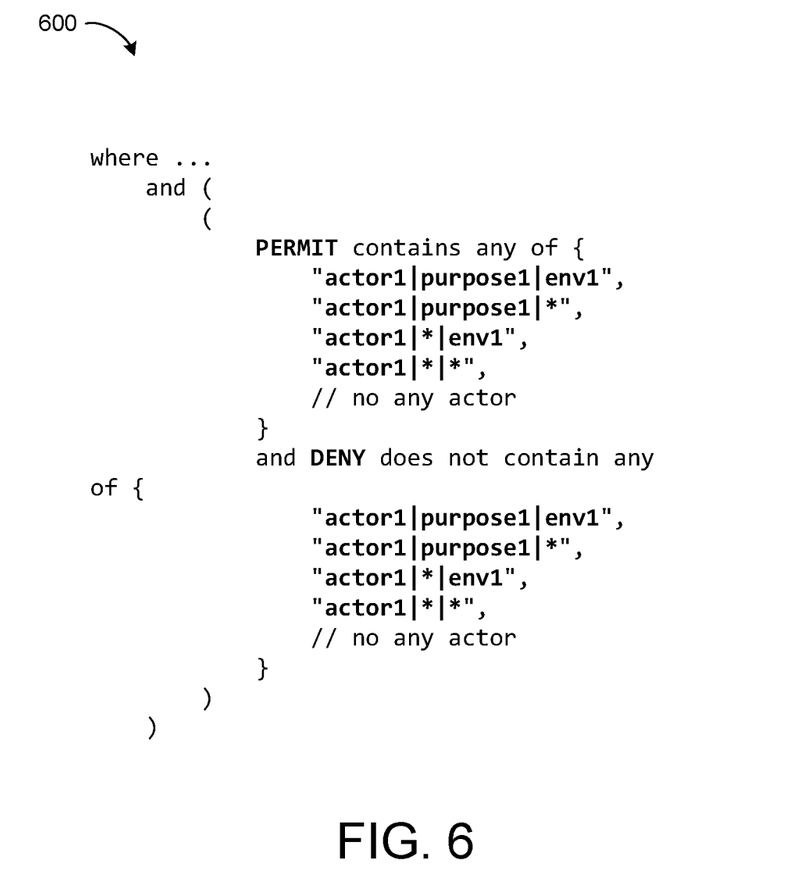
FIG. 6 is an example search filter that may be used to perform an indexed search of consent-indexed healthcare data.

FIG. 6 is code for an example search filter 600 that may be executed to perform an indexed search of the consent-indexed healthcare data 300. In the illustrated example, the search engine 230 generates the search filter 600 based on an asserted access consent scenario, such as:

actors: {"actor1", "actor2"}, purposes: {"purpose1"}, envs: {"env1"}.

Because the asserted consent scenario includes various combinations of the asserted actors, purpose and environment, the search engine 230 generates a corresponding set of potential asserted access consent scenarios that includes:

{"actor1|purpose1|env1", "actor1|purpose1|*", "actor1|*|env1", "actor1|*|*", "actor2|purpose1|env1", "actor2|purpose1|*" "actor2|*|env1", "actor2|*|*"}.

The search engine 230 then generates the search filter 600 such that these access consent scenarios are permitted, and other consent scenarios are denied. In some examples, the search filter 600 is encoded in JavaScript Object Notation (JSON) to enable efficient execution of the requested indexed search.

Referring back to FIG. 1, in some examples, the system 100 assumes a zero trust configuration such that the system 100 includes an authenticator 150 to authenticate users (e.g., the patient 102, the administrator 104, and the accessee 106) of the healthcare data storage system 110. In some implementations, even when the authenticator 150 authenticates a user, the access control system 200 (re-)confirms the authentication of a user based on credentials provided by the user and the authenticator 150.

While the example of FIG. 1 shows a single patient 102 and a single accessee 106, it should be understood that the system 100 and the storage system 110 may store healthcare data 300 and consent directives 400 for hundreds millions of patients 102, and may handle access requests from millions of actors.

Turning to FIG. 2, the access control system 200 executes a proxy 240 to, in response to the access control system 200 receiving an FHIR API search request 20 for particular requested healthcare data that includes a consent token 27, validate the consent token's signature, expiry, and/or other parameters. If the consent token 27 is valid, the proxy 240 converts the received FHIR API search request 20 to an HTTP search request 28 (e.g., in JSON) having an HTTP search request header 29, such as:

GET
https://healthcare.googleapis.com/v1/projects/PROJECT_ID/locations/L OCATION/datasets/DATASET_ID/fhirStores/FHIR_STORE_ID/fhir/ . . .
HTTP/1.1 X-Consent-Scope: actor/actor1 actor/actor2 purp/purpose1 env/env1

Here, the parameters of the consent token 27 (i.e., actor/actor1 actor/actor2 purp/purpose1 env/env1) are included in the HTTP search request header 29. The HTTP search request 28 includes the search payload (e.g., identify particular requested healthcare data) from the received FHIR API search request 20. The proxy 240 may also reverse proxy the FHIR API request.

In some implementations, the access control system 200 is based on zero trust and executes an authenticator 250 to (re-)authenticate a user (even when authenticated by the authenticator 150) before they are enabled to perform a search of the healthcare data 300.

The access control system 200 also executes data collection 260 to ingest healthcare data from the data sources 140 into the healthcare data 300, and to add, update and/or delete consent directives 400.

Figure 7:
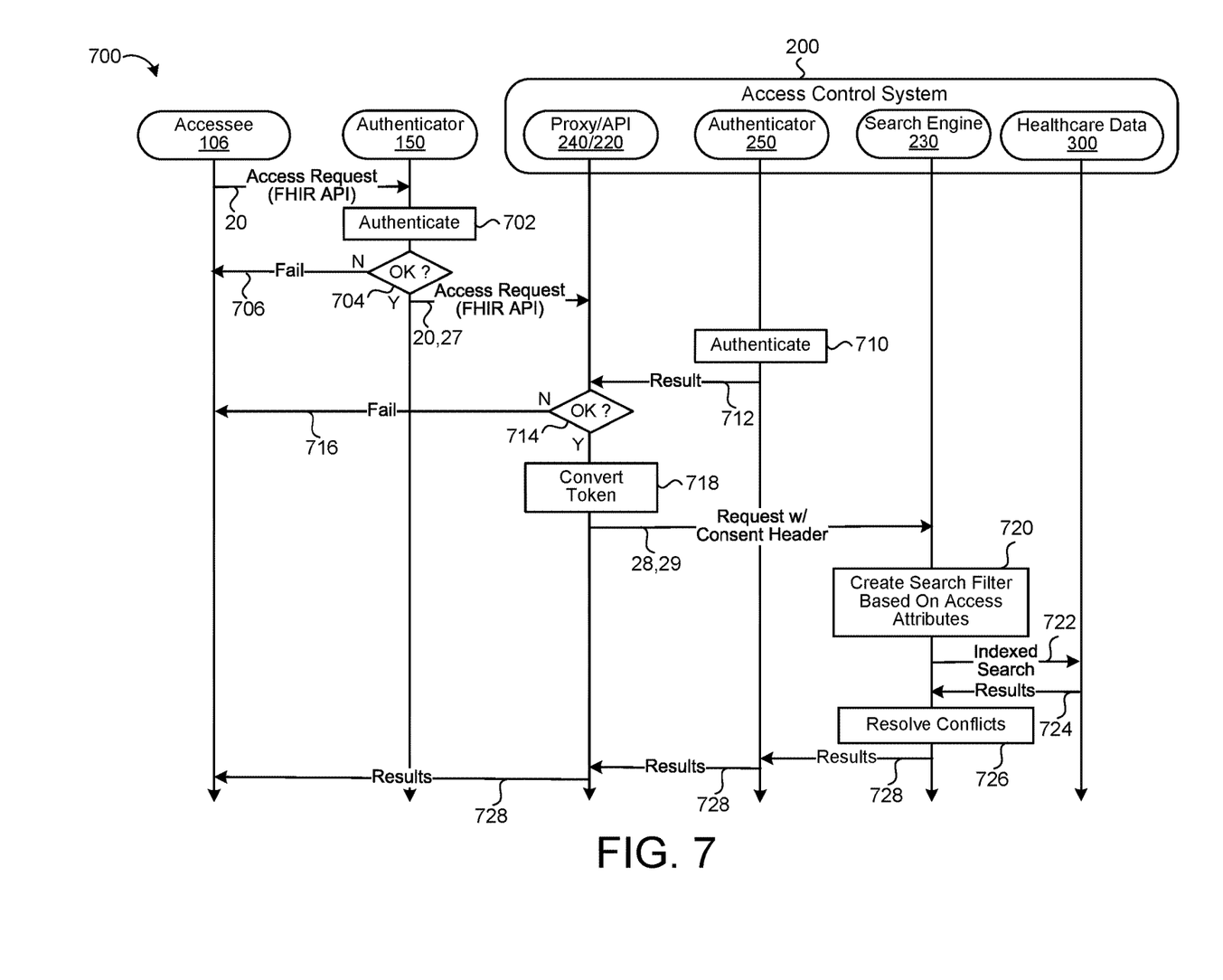
FIG. 7 is a graph showing a detailed operation of the healthcare data system of FIG. 1.

FIG. 7 is a graph 700 showing detailed operations of the system 100 for performing a request to search for healthcare data. The example of FIG. 7 starts with the accessee 106 using the computing device 120c to send an FHIR API search request 20 including a consent token 27 via the authenticator 150. The consent token 27 includes one or more consent parameters 21 that represent one or more presently asserted access consent scenarios for the search request 20. The consent parameters 21 may include/indicate at least one of an actor identifier for the accessee 106 providing the search request 20, a purpose identifier for requesting healthcare data, an environment identifier identifying an environment for the accessee 106, or a timestamp indicating a time/date of the search request 20.

The authenticator 150 attempts to authenticate the accessee 106 (block 702). If the accessee 106 is not successfully authenticated (block 704), the authenticator 150 returns a fail notification 706 to the accessee 106. Otherwise, the FHIR API search request 20 with a consent token 27 is forwarded to the access control system 200.

At the access control system 200, the authenticator 250 attempts to (re-)authenticate the accessee 106 (block 710), and sends a result 712 of the authentication to the API 220. If not successfully authenticated (block 714), the API 220 returns a fail notification 716 to the accessee 106, and terminates the search request 20.

Otherwise (block 714), the proxy 240 converts the consent token 27 of the FHIR API search request 20, if valid, to an HTTP search request header 29 (block 718). The proxy 240 sends an HTTP search request 28 containing the HTTP search request header 29 to the search engine 230.

The search engine 230 generates a search filter 600 based on the header 29 of the HTTP search request 28 (block 720), and performs an indexed search of the consent-indexed healthcare data 300 using the search filter 600 to obtain search results 724. As needed, the search engine 230 resolves any conflicts (block 726) and forwards final results 728 of the search to the accessee 106.

Figure 8:
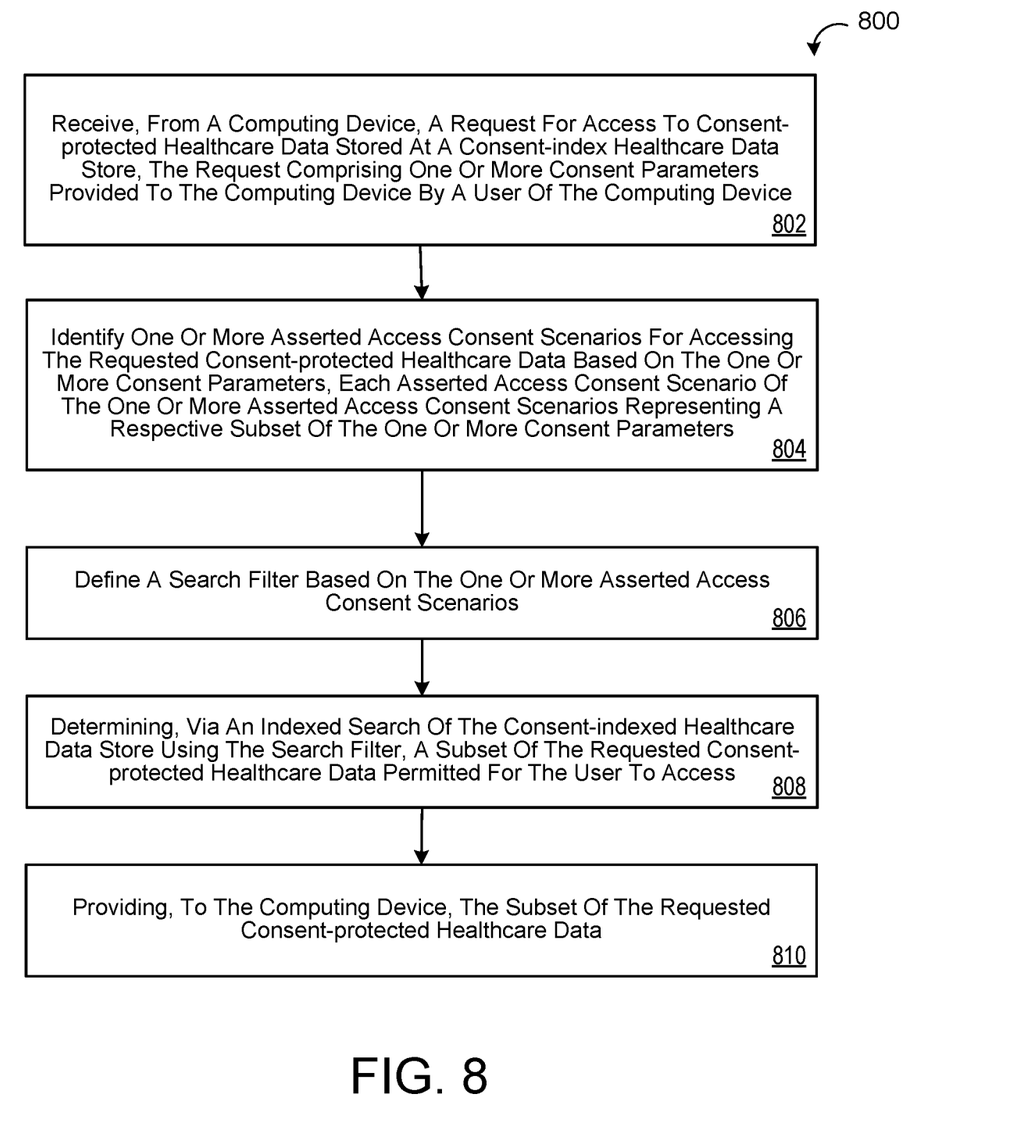
FIG. 8 is a flowchart of an exemplary arrangement of operations for a method of performing index searching of consent-protected private healthcare data.

FIG. 8 is a flowchart of an exemplary arrangement of operations for a method 800 of performing a consent-based search of consent-protected healthcare data. The method 800, at operation 802, receives, from a computing device 102c, a search request for access to consent-protected healthcare data 300. The search request 20 includes one or more consent parameters 21 provided to the computing device 120c by a user (i.e., the accessee 106) of the computing device 120c. The consent parameters 21 may include/indicate at least one of an actor identifier for the accessee 106 providing the search request 20, a purpose identifier for requesting healthcare data, an environment identifier identifying an environment for the accessee 106, or a timestamp indicating a time/date of the search request 20.

At operation 804, the method 800 identifies one or more asserted access consent scenarios for accessing the requested consent-protected healthcare data 300 based on the one or more consent parameters 21. Each asserted access consent scenario of the one or more asserted access consent scenarios represents a respective subset of the one or more consent parameters 21.

The method 800, at operation 806, defines a search filter 600 based on the one or more asserted access consent scenarios. At operation 808, the method 800 includes determining, via an indexed search 722 of the consent-indexed healthcare data 300 using the search filter 600, a subset of the requested consent-protected healthcare data 300 (i.e., the results 26) permitted for the user (i.e., the accessee 106) to access. The method 800, at operation 810, provides, to the computing device 102c, the subset of the requested consent-protected healthcare data.

Figure 9:
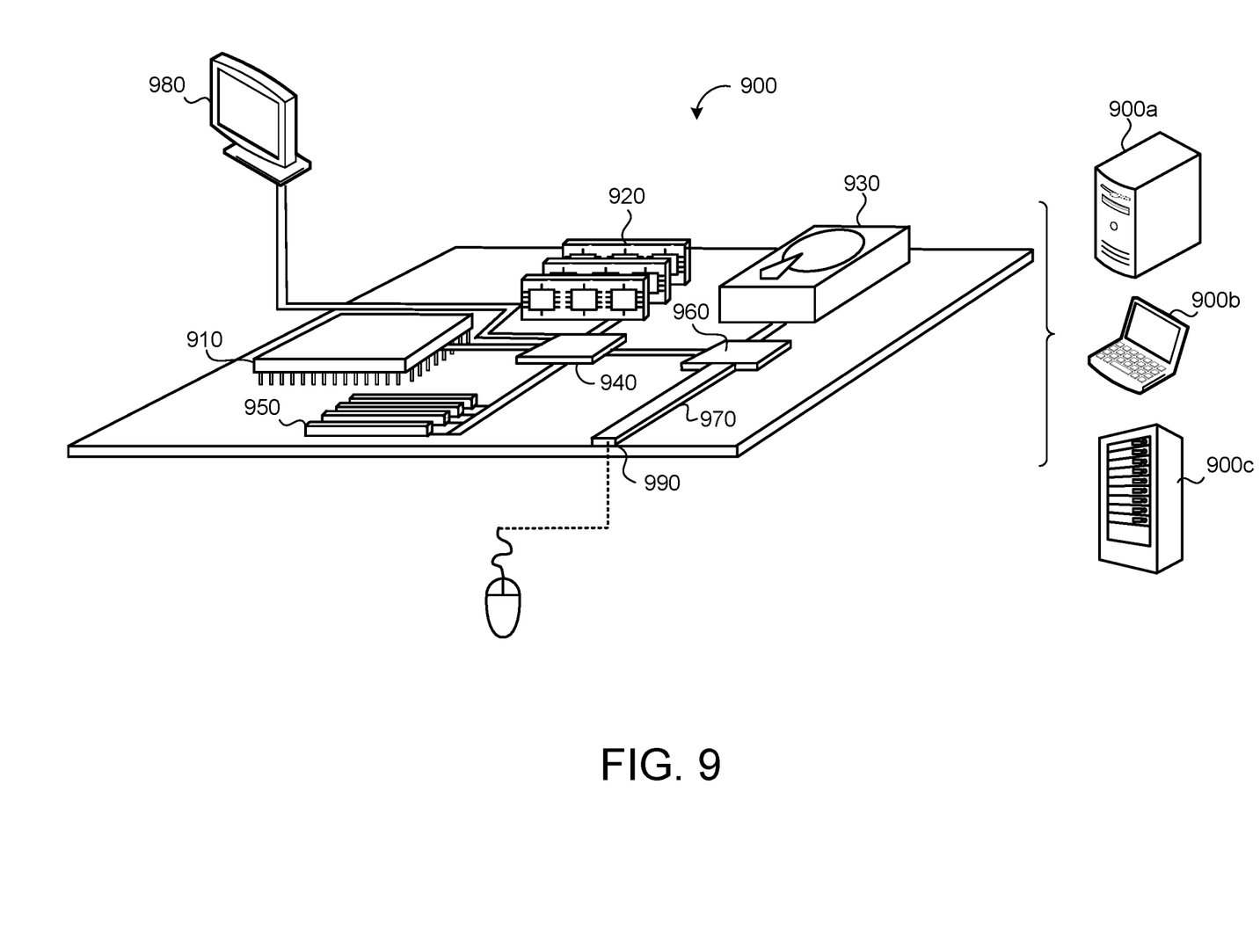
FIG. 9 is a schematic view of an example computing device that may be used to implement the systems and methods described herein.

FIG. 9 is a schematic view of an example computing device 900 that may be used to implement the systems and methods described in this document. The computing device 900 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 900 includes a processor 910 (i.e., data processing hardware) that can be used to implement the data processing hardware 112 and 122, memory 920 (i.e., memory hardware) that can be used to implement the storage hardware 114 and 124, a storage device 930 (i.e., memory hardware) that can be used to implement the storage hardware 114, 118, and 124, a high-speed interface/controller 940 connecting to the memory 920 and high-speed expansion ports 950, and a low speed interface/controller 960 connecting to a low speed bus 970 and a storage device 930. Each of the components 910, 920, 930, 940, 950, and 960, are interconnected using various busses, and may be mounted on a common motherboard or in other manners as appropriate. The processor 910 can process instructions for execution within the computing device 900, including instructions stored in the memory 920 or on the storage device 930 to display graphical information for a graphical user interface (GUI) on an external input/output device, such as display 980 coupled to high speed interface 940. The processor 910 may refer to a computing processing unit (CPU), a graphical processing unit (GPU), a tensor processing unit (TPU) or any combination of the three. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 920 stores information non-transitorily within the computing device 900. The memory 920 may be a computer-readable medium, a volatile memory unit(s), or non-volatile memory unit(s). The non-transitory memory 920 may be physical devices used to store programs (e.g., sequences of instructions) or data (e.g., program state information) on a temporary or permanent basis for use by the computing device 900. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 930 is capable of providing mass storage for the computing device 900. In some implementations, the storage device 930 is a computer-readable medium. In various different implementations, the storage device 930 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 920, the storage device 930, or memory on processor 910.

The high speed controller 940 manages bandwidth-intensive operations for the computing device 900, while the low speed controller 960 manages lower bandwidth-intensive operations. Such allocation of duties is exemplary only. In some implementations, the high-speed controller 940 is coupled to the memory 920, the display 980 (e.g., through a graphics processor or accelerator), and to the high-speed expansion ports 950, which may accept various expansion cards (not shown). In some implementations, the low-speed controller 960 is coupled to the storage device 930 and a low-speed expansion port 990. The low-speed expansion port 990, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, the computing device 900 may be implemented as a standard server 900*a* or multiple times in a group of such servers 900*a*, as a laptop computer 900*b*, or as part of a rack server system 900*c*.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Unless expressly stated to the contrary, the phrase "at least one of A, B, or C" is intended to refer to any combination or subset of A, B, C such as: (1) at least one A alone; (2) at least one B alone; (3) at least one C alone; (4) at least one A with at least one B; (5) at least one A with at least one C; (6) at least one B with at least C; and (7) at least one A with at least one B and at least one C. Moreover, unless expressly stated to the contrary, the phrase "at least one of A, B, and C" is intended to refer to any combination or subset of A, B, C such as: (1) at least one A alone; (2) at least one B alone; (3) at least one C alone; (4) at least one A with at least one B; (5) at least one A with at least one C; (6) at least one B with at least one C; and (7) at least one A with at least one B and at least one C.

A number of implementations have been described. Nevertheless, it will be understood that various modifications may be made without departing from the spirit and scope of the disclosure. Accordingly, other implementations are within the scope of the following claims.

What is claimed is:

1. A computer-implemented method executed by data processing hardware that causes the data processing hardware to perform operations comprising:
   receiving, from a computing device, a search request for access to consent-protected healthcare data stored at a consent-indexed healthcare data store in communication with the data processing hardware, the search request comprising one or more consent parameters asserted for a user of the computing device;
   identifying one or more asserted access consent scenarios for accessing the requested consent-protected healthcare data based on the one or more consent parameters, each respective asserted access consent scenario of the one or more asserted access consent scenarios representing a respective subset of the one or more consent parameters;
   defining a search filter based on the one or more asserted access consent scenarios;
   determining, via an indexed search of the consent-indexed healthcare data store using the search filter, a subset of the requested consent-protected healthcare data permitted for the user to access;
   determining that particular healthcare data of the requested consent-protected healthcare data is included within the subset when the indexed search both permits and denies access to the particular consent-protected healthcare data; and
   providing, to the computing device, the subset of the requested consent-protected healthcare data.

2. The method of claim 1, wherein the one or more consent parameters comprise at least one of an actor identifier for the user, a purpose identifier for requesting the requested consent-protect healthcare data, an environment identifier identifying an environment for the user, or a timestamp indicating a time/date of the search request.

3. The method of claim 1, wherein the one or more consent parameters are provided by the user via the computing device and/or determined by the data processing hardware based on one or more attributes of the user or the computing device.

4. The method of claim 1, wherein the consent-indexed healthcare data store comprises a plurality of healthcare data records indexed based on consent scenarios.

5. The method of claim 4, wherein each consent scenario of the consent scenarios represents two or more of an actor, a purpose, an environment, or a time period.

6. The method of claim 1, wherein the consent-indexed healthcare data store comprises a plurality of healthcare data records, each healthcare data record of the plurality of healthcare data records comprising:
   a respective permit field defining one or more respective access consent scenarios that permit access to the healthcare data record; and
   a respective deny field defining one or more respective access consent scenarios that deny access to the healthcare data record.

7. The method of claim 6, wherein each asserted access consent scenario of the plurality of asserted access consent scenarios represents two or more of an actor, a purpose, an environment, or a time period.

8. The method of claim 1, wherein the request comprises:
   an indication that an identity of the user of the computing device has been authenticated; and
   a fast healthcare interoperability resources (FHIR) application programming interface (API) token comprising the one or more consent parameters.

9. The method of claim 8, wherein the operations further comprise, in response to receiving the request, re-authenticating the identity of the user of the computing device.

10. The method of claim 8, wherein the operations further comprise providing a proxy to convert the FHIR API token to a hypertext transfer protocol (HTTP)-based consent header.

11. A system comprising:
    data processing hardware; and
    memory hardware in communication with the data processing hardware, the memory hardware storing instructions that, when executed on the data processing hardware, cause the data processing hardware to perform operations comprising:
- receiving, from a computing device, a search request for access to consent-protected healthcare data stored at a consent-indexed healthcare data store in communication with the data processing hardware, the search request comprising one or more consent parameters asserted for a user of the computing device;
- identifying one or more asserted access consent scenarios for accessing the requested consent-protected healthcare data based on the one or more consent parameters, each respective asserted access consent scenario of the one or more asserted access consent scenarios representing a respective subset of the one or more consent parameters;
- defining a search filter based on the one or more asserted access consent scenarios;
- determining, via an indexed search of the consent-indexed healthcare data store using the search filter, a subset of the requested consent-protected healthcare data permitted for the user to access;
- determining that particular healthcare data of the requested consent-protected healthcare data is included within the subset when the indexed search both permits and denies access to the particular consent-protected healthcare data; and
- providing, to the computing device, the subset of the requested consent-protected healthcare data.

12. The system of claim 11, wherein the one or more consent parameters comprise at least one of an actor identifier for the user, a purpose identifier for requesting the requested consent-protect healthcare data, an environment identifier identifying an environment for the user, or a timestamp indicating a time/date of the search request.

13. The system of claim 11, wherein the one or more consent parameters are provided by the user via the computing device and/or determined by the data processing hardware based on one or more attributes of the user or the computing device.

14. The system of claim 11, wherein the consent-indexed healthcare data store comprises a plurality of healthcare data records indexed based on consent scenarios.

15. The system of claim 14, wherein each consent scenario of the consent scenarios represents two or more of an actor, a purpose, an environment, or a time period.

16. The system of claim 11, wherein the consent-indexed healthcare data store comprises a plurality of healthcare data records, each healthcare data record of the plurality of healthcare data records comprising:
- a respective permit field defining one or more respective access consent scenarios that permit access to the healthcare data record; and
- a respective deny field defining one or more respective access consent scenarios that deny access to the healthcare data record.

17. The system of claim 16, wherein each asserted access consent scenario of the plurality of asserted access consent scenarios represents two or more of an actor, a purpose, an environment, or a time period.

18. The system of claim 11, wherein the request comprises:
- an indication that an identity of the user of the computing device has been authenticated; and
- a fast healthcare interoperability resources (FHIR) application programming interface (API) token comprising the one or more consent parameters.

19. The system of claim 18, wherein the operations further comprise, in response to receiving the request, re-authenticating the identity of the user of the computing device.

20. The system of claim 18, wherein the operations further comprise providing a proxy to convert the FHIR API token to a hypertext transfer protocol (HTTP)-based consent header.

* * * * *